(12) United States Patent
Salafsky et al.

(10) Patent No.: US 6,953,694 B2
(45) Date of Patent: Oct. 11, 2005

(54) ATTACHMENT OF SECOND HARMONIC-ACTIVE MOIETY TO MOLECULES FOR DETECTION OF MOLECULES AT INTERFACES

(75) Inventors: Joshua S. Salafsky, New York, NY (US); Kenneth B. Eisenthal, Ridgewood, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/731,366

(22) Filed: Dec. 6, 2000

(65) Prior Publication Data

US 2002/0094520 A1 Jul. 18, 2002

(51) Int. Cl.⁷ ......................... G01N 21/00; G01N 33/53
(52) U.S. Cl. ...................... 436/164; 436/501; 436/518; 435/6; 435/7.92; 356/300
(58) Field of Search ................................. 436/501, 164, 436/172, 505, 800, 518; 435/5, 7.1, 6, 7.92; 422/82.05–82.09; 356/300, 318

(56) References Cited

U.S. PATENT DOCUMENTS

| | | | | |
|---|---|---|---|---|
| 5,145,790 A | * | 9/1992 | Mattingly et al. | 436/536 |
| 5,236,826 A | * | 8/1993 | Marshall et al. | 435/7.92 |
| 5,696,157 A | * | 12/1997 | Wang et al. | 514/457 |
| 5,962,248 A | * | 10/1999 | Tadano et al. | 435/22 |
| 6,055,051 A | * | 4/2000 | Eisenthal et al. | 356/518 |
| 6,180,415 B1 | * | 1/2001 | Schultz et al. | 436/518 |
| 6,194,222 B1 | * | 2/2001 | Buechler et al. | 436/518 |
| 6,456,423 B1 | * | 9/2002 | Nayfeh et al. | 359/328 |
| 2002/0094528 A1 | | 7/2002 | Salafsky | |
| 2002/0127563 A1 | | 9/2002 | Salafsky | |

FOREIGN PATENT DOCUMENTS

| GB | 0740156 | * 11/1996 |
|---|---|---|
| WO | WO 02/44412 A1 | 6/2002 |

OTHER PUBLICATIONS

Conboy et al, Journal of Phsical Chemistry, Studies of Alkane/Water Interfaces by Total Internal Reflection Second Harmonic Generation. 1994, 98, 9688–9692.*
Khatchatouriants, A. et al (2000) "GFP Is a Selective Non-Linear Optical Sensor of Electrophysiological Processes in *Caenorhabditis elegans*," Biophysical Journal 79:2345–2352 (Exhibit 1),.
Lewis, A. et al (1999) "Second–harmonic generation of biological interfaces: probing the membrane protein bacteriorhodopsin and imaging membrane potential around GFP molecules at specific sites in neuronal cells of *C. elegans*." Chemical Physics 245: 133–144 (Exhibit 2); and.

Peleg, G. et al (1999) "Nonlinear optical measurement of membrane potential around single molecules at selected cellular sites," Proc. Natl. Acad. Sci. USA 96:6700–6704 (Exhibit 3).

Campagnola, P.J. et al. High–Resolution Nonlinear Optical Imaging of Live Cells by Second Harmonic Generation. *Biophysical Journal* (1999) 77: 3341–3349.

Eisenthal, K.B. Photochemistry and photophysics of liguid interfaces by second harmonic spectroscopy. *J. Phys. Chem.* (1996) 100: 12997–13006.

Peleg, G., et al. Nonlinear optical measurement of membrane potential around single molecules at selected cellular sites. *Proc. Natl. Acad. Sci.* (1999) 96: 6700–6704.

Salafsky, J.S and Eisenthal, K.B. Protein Adsorption at Interfaces Detected by Second Harmonic Generation. *J. Phys. Chem. B* (2000) 104: 7752–7755.

Salafsky, J.S. and Eisenthal, J.B. Second harmonic spectroscopy: detection and orientation of molecules at a biomembrane interface. *Chemical Physical Letters* (2000) 319: 435–439.

Srivastava, A. and Eisenthal, K.B. Kinetics of molecular transport across a liposome bilayer. *Chemical Physical Letters* (1998) 292: 345–351.

European Search Report issued May 18, 2005 in connection with European Patent Application No. 01995403.1

Ditcham, W.G.F. et al., "An immunosensor with potential for the detetion of viral antigens in body fluids, based on...", Biosensors and Bioelectronics, 16(3):221–224 (2001).

Rinuy, J. et al., "Second harmonic generation of glucose oxidase at the air/water interface", Biophys. Jour., 77(6):3350–3355 (1999).

Wang, H. et al., "In Situ, Nonlinear Optical Probe of Surfactant Adsorption on the Surface...", Langmuir, ACS, Washington, DC, US, 16(6):2475–2481 (2000).

* cited by examiner

*Primary Examiner*—Long V. Le
*Assistant Examiner*—Gary W. Counts
(74) *Attorney, Agent, or Firm*—John P. White, Esq.; Cooper & Dunham LLP

(57) ABSTRACT

This invention provides methods of detecting molecules at an interface, which comprise labeling the molecules with a second harmonic-active moiety and detecting the labeled molecules at the interface using a surface selective technique. The invention also provides methods for detecting a molecule in a medium and for determining the orientation of a molecular species within a planar surface using a second harmonic-active moiety and a surface selective technique.

34 Claims, 4 Drawing Sheets

ATTACHMENT OF SECOND HARMONIC-ACTIVE MOIETY TO MOLECULES FOR DETECTION OF MOLECULES AT INTERFACES

Government support under grant number CHE-96-12685 from the National Science Foundation and grant numbers DE-FG02-91ER and DE-FG02-14226 from the Department of Energy. Accordingly, the U.S. Government has certain rights in this invention.

BACKGROUND OF THE INVENTION

Throughout this application, various publications are referenced in parentheses by author and year. Full citations for these references may be found at the end of the specification immediately preceding the claims. The disclosures of these publications in their entireties are hereby incorporated by reference into this application to more fully describe the state of the art to which this invention pertains.

Second harmonic generation (SHG) is a powerful spectroscopic tool for studying interfacial regions at the molecular scale, but to date has been confined mainly to non-biological systems. Recently, however, SHG has been extended to the study of a SH-active moiety at a supported lipid membrane system (Salafsky and Eisenthal, 2000a), a useful model for biological studies, and to the detection of protein adsorption at charged interfaces through the indirect effect the protein has on polarized water molecules near the surface (Salafsky and Eisenthal, 2000b). Direct detection of molecules such as proteins at interfaces could be useful in a number of biological studies, for example in studies of protein-receptor binding at a membrane or cellular interface or in the development of biosensors, but is hindered by the intrinsically low SH cross-section of proteins. For detection of molecules by SHG, the SH-active moiety must possess a hyperpolarizability and a net orientation at the interface. Although some proteins do contain chromophoric cofactors which are SH-active, their absorption is usually quite low or they are centrosymmetric. Other sources of SH activity in proteins include the aromatic amino acid side chains which are weakly SH-active. However, their varying orientations within the protein would reduce any SH signal.

The present application discloses the concept and technique of a 'SHG-label'. SHG labels are second harmonic-active moieties which can be attached to a molecule or particle of interest that is not SH-active or only weakly SH-active, in order to render the molecule amenable to study at an interface. The labeled molecules may then be studied by surface-selective techniques such as second harmonic generation or sum-frequency generation. The technique can be illustrated by covalently labeling a protein, cytochrome c, with a SH-active moiety which is specific for either amine or sulfhydryl groups, common chemical moieties which exist on the surface of many protein molecules as part of their amino acid side-chains. Unlike detection with fluorescent labels, SHG-labels have the important advantage that only labeled proteins at an interface, and with a net orientation, contribute to the second harmonic signal; labeled protein molecules in the bulk contribute no signal. Furthermore, unlabeled molecules at the interface are undetectable. SHG-labels should find use in a variety of biological applications including studies of protein-protein, protein-membrane, and cell-cell interactions. SHG-labels can also be used to study other systems such as nanoparticle surfaces and polymer systems (polymer beads). In turn the labelled nanoparticle or labelled polymer bead can be used for example as a sensor of molecules in the surrounding medium.

SUMMARY OF THE INVENTION

The present invention provides a method for detecting a molecule at an interface, which comprises labeling the molecule with a second harmonic-active moiety and detecting the labeled molecule at the interface using a surface selective technique.

The invention also provides a method for detecting a molecule in a medium, which comprises:
(a) labeling a surface with a second harmonic-active moiety wherein the second harmonic-active moiety specifically interacts with the molecule to be detected,
(b) exposing the surface to the medium thereby creating an interface at the surface,
(c) detecting the second harmonic-active moiety at the interface by measuring a signal generated using a surface selective technique, and
(d) detecting a change in the signal when the molecule interacts with the second harmonic-active moiety, thereby detecting the molecule in the medium.

This invention provides a method for determining the orientation of a molecular species within a planar surface, which comprises:
(a) labeling the species with a second harmonic-active moiety which specifically binds to the species;
(b) determining the orientation of the second harmonic-active moiety with respect to the species;
(c) measuring the polarization of second-harmonic light to determine the orientation of the second harmonic-active moiety with respect to the planar surface; and
(d) determining the orientation of the species within the planar surface from the orientation of the moiety with respect to the surface as determined in step (c) and from the orientation of the moiety with respect to the species as determined in step (b).

DETAILED DESCRIPTION OF THE INVENTION

Figure 1:
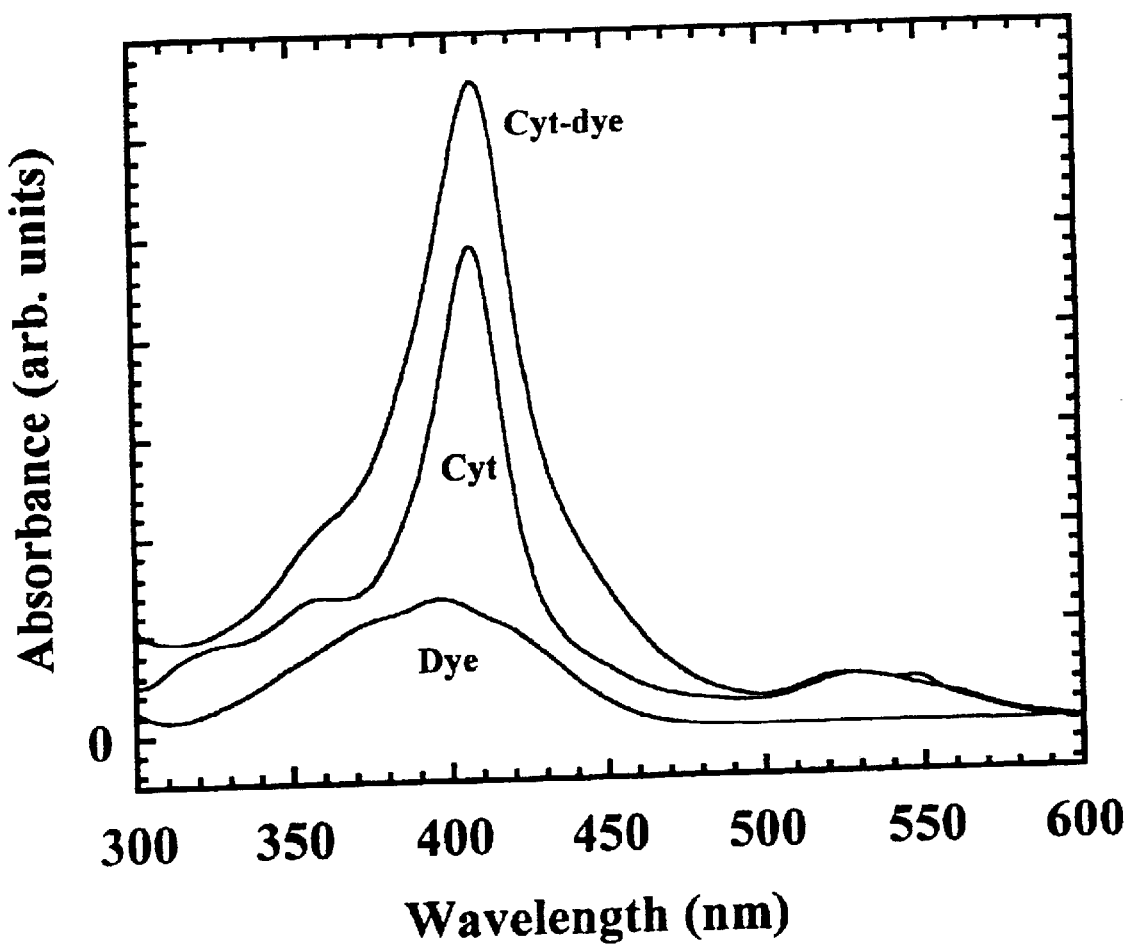
FIG. 1. Absorption spectra of the SH-active moiety (dye) (oxazole derivative), cytochrome (cyt) c and dye-cyt c (amine) conjugate. The SH-active moiety is covalently attached to amine groups on the protein's surface and, from the absorbance and known extinction coefficients, is bound at a mole ratio of 1.5:1 (dye:protein) in the conjugate.

The following definitions are presented as an aid in understanding this invention.

As used herein second harmonic refers to a frequency of light that is twice the frequency of a fundamental beam of light. A second harmonic-active moiety is a substance which when irradiated with a fundamental beam of light generates a second harmonic of the fundamental.

Having due regard to the preceding definitions, the present invention concerns a method for detecting a molecule at an interface, which comprises labeling the molecule with a second harmonic-active moiety and detecting the labeled molecule at the interface using a surface selective technique.

In different embodiments of the invention, the surface selective technique is second harmonic generation or sum-frequency generation. Sum frequency generation (SFG) is a nonlinear, optical technique whereby light at one frequency ($\omega_1$) is mixed with light at another frequency ($\omega_2$) to yield a response at the sum frequency ($\omega_1+\omega_2$) (Shen, 1984, 1989). SFG is particularly useful for the detection of molecules at surfaces through their characteristic vibrational transitions and, in this case, is essentially a surface-selective infrared spectroscopy with $\omega_1$ and $\omega_2$ at visible and infrared frequencies.

In different embodiments of the invention, the molecule to be detected is a protein, a nucleic acid, a lipid, or a carbohydrate. In different embodiments, the nucleic acid is a ribonucleic acid (RNA) or a deoxyribonucleic acid (DNA). In different embodiments, the DNA is genomic DNA or cDNA.

In different embodiments, the molecule to be detected is a pollutant or other environmentally important molecule.

In different embodiments, the molecule is on a surface of a nanoparticle or a polymer bead.

In different embodiments, the second harmonic-active moiety is bound to the molecule by a specific interaction or by a non-specific interaction. In different embodiments, the specific interaction comprises a covalent bond or a hydrogen bond. In different embodiments, the second harmonic-active moiety is specific for an amine group or for a sulfhydryl group on the molecule to be detected. In one embodiment, the non-specific interaction comprises an electrostatic interaction.

In one embodiment, the second harmonic-active moiety comprises a plurality of individual second harmonic-active labels which each have a nonlinear susceptibility and are bound together in a fixed and determinate orientation with respect to each other so as to increase the overall nonlinear susceptibility of the second harmonic-active moiety.

In different embodiments, the interface is at a membrane, a liposome, a cell surface, a viral surface, a bacterial surface, or a biosensor. In different embodiments, the interface is a vapor-liquid interface, a liquid-liquid interface, a liquid-solid, or a solid-solid interface. In one embodiment, the vapor-liquid interface is an air-water interface. In one embodiment, the liquid-liquid interface is an oil-water interface. In different embodiments, the liquid-solid interface is a water-glass interface or a benzene-$SiO_2$ interface.

The present invention provides for the use of any of the methods described herein to detect binding of a protein to a receptor on a membrane. The invention also provides for the use of any of the methods described herein to detect binding of a virus to a cell. The invention further provides for the use of any of the methods described herein to study protein-protein interaction at an interface or to study cell-cell interaction.

The invention provides a method for detecting a molecule in a medium, which comprises:
(a) labeling a surface with a second harmonic-active moiety wherein the second harmonic-active moiety specifically interacts with the molecule to be detected,
(b) exposing the surface to the medium thereby creating an interface at the surface,
(c) detecting the second harmonic-active moiety at the interface by measuring a signal generated using a surface selective technique, and
(d) detecting a change in the signal when the molecule interacts with the second harmonic-active moiety, thereby detecting the molecule in the medium.

In different embodiments of the method, the surface is on a nanoparticle or a polymer bead. In different embodiments, the surface selective technique is second harmonic generation or sum-frequency generation.

In different embodiments, the molecule to be detected is a pollutant or a charged species. In different embodiments, the pollutant is lead or polychlorinated biphenyl. In one embodiment, the charged species is a chloride ion.

In one embodiments, the interaction between the second harmonic-active moiety and the molecule to be detected is an antibody-antigen interaction.

In different embodiments, the medium contains an amount of the molecule to be detected, the change in the signal when the molecule interacts with the second harmonic-active moiety is a quantitative change, and the amount of the molecule in the medium can be determined from the change in the signal.

This invention provides a method for determining the orientation of a molecular species within a planar surface, which comprises:
(a) labeling the species with a second harmonic-active moiety which specifically binds to the species;
(b) determining the orientation of the second harmonic-active moiety with respect to the species;
(c) measuring the polarization of second-harmonic light to determine the orientation of the second harmonic-active moiety with respect to the planar surface; and
(d) determining the orientation of the species within the planar surface from the orientation of the moiety with respect to the surface as determined in step (c) and from the orientation of the moiety with respect to the species as determined in step (b).

In one embodiment of the method, the orientation of the second harmonic-active moiety with respect to the species is determined using x-ray crystallography. In different embodiments, the planar surface is selected from the group consisting of an organic material surface, an inorganic material surface, a polymeric material surface, a mineral surface, a clay surface, a biological membrane surface, and a synthetic membrane surface. In different embodiments, the molecular species is selected from the group consisting of an organic species, an inorganic species, a polymeric species, a protein, a lipid, a nucleic acid, and a carbohydrate.

This invention will be better understood from the Experimental Details which follow. However, one skilled in the art will readily appreciate that the specific methods and results discussed are merely illustrative of the invention as described more fully in the claims which follow thereafter.

Experimental Details

The attachment of a second harmonic-active moiety to a molecule for detection of the molecule at an interface can be illustrated by studying SHG-labeled cytochrome c at the air-water interface. Since the x-ray crystal structure of cytochrome c has been solved to atomic resolution, experiments can be designed to randomly or selectively label various amino acid side-chains on the protein's surface. For instance, because only one surface cysteine exists on cytochrome c, SHG can be used to detect the orientation of the cysteine conjugate at the air-water interface through a null angle technique. The free energy of adsorption of the SH-active moiety-protein conjugate to the air-water interface can also be measured.

Theoretical Considerations

The production of second harmonic light from an interface can be described by the following equation:

$$I(2\omega) = \frac{32\pi^3\omega^2 \sec^2\Theta}{c^3\varepsilon(\omega)\varepsilon^{1/2}(2\omega)} |\vec{e}(2\omega)\cdot\chi^{(2)}:\vec{e}(\omega)\vec{e}(\omega)|^2 I^2(\omega) \quad (1)$$

where $I(2\omega)$ and $I(\omega)$ are the intensity of the second harmonic and fundamental light, respectively, $\chi^{(2)}$ is the second-order nonlinear susceptibility tensor, $\vec{e}(\omega)$ and $\vec{e}(2\omega)$ the products of the Fresnel factors and the polarization vectors for the light beams, c is the speed of light, $\varepsilon$ is the index of refraction, and $\Theta$ is the angle between the reflected harmonic light and the surface plane (Heinz, 1991). The surface nonlinear susceptibility $\chi^{(2)}$, neglecting local-field effects, is $$\chi^{(2)} = N_s <\alpha^{(2)}> \quad (2)$$

where $N_s$ is the total number of molecules per unit area at the interface and $<\alpha^{(2)}>$ is the average over the orientational distribution of the nonlinear polarizabilities in these molecules. Equation (2) can be more explicitly expressed as $$\chi_{ijk}^{(2)} = N_s <T_{i\lambda}T_{j\mu}T_{k\nu}> \alpha_{\lambda\mu\nu}^{(2)} \quad (3)$$

following Reider and Heinz (1995), where $\alpha^{(2)}_{i'j'k'}$ refers to the molecular nonlinear polarizability in the coordinate system of the molecule, $T_{i\lambda}$ is the transformation tensor which relates the laboratory and molecular frames of reference, and the average is taken over the orientational distribution of the molecules at the interface. From equations 1 and 2, the intensity of second harmonic radiation is quadratic with the surface density $N_s$ of aligned molecules.

In the use of SHG-labels for molecules (nonlinear polarizability $\alpha_L^{(2)}$ per label), the distribution of the labels will determine the orientational average of the labels' polarizability and therefore the SH intensity. Typically, the labels will not be oriented in the same direction, and so the SH intensity will be reduced; in the limit of many randomly distributed labels, the SH intensity will approach zero. Labeling ratios can therefore be adjusted according to the particular molecule under study to maximize the net SH signal from several labels. One could also use 'super-labels', in which a number of individual labels are bound together in a fixed and determinate orientation with respect to each other, in order to maximize the overall hyperpolarizability. The molecules, and therefore the labels, must also exhibit a net orientation at the interface to produce a nonlinear effect. This requirement could be an advantage, however, in detecting specific interactions, for example with protein-receptor recognition which leads to a net protein orientation. Furthermore, through mutagenesis, one can specifically engineer proteins for the purpose of placing SHG-labels in pre-determined positions.

Methods

Amine- and sulfhydryl-specific dyes (Molecular Probes; Eugene, Oreg.), derivatives of an oxazole dye which has been shown to be highly SH-active, were covalently attached to cytochrome c via either a surface lysine or cysteine amino acid, respectively. Cytochrome c (Horse heart, Sigma) is a soluble, globular protein of about 12 kDa molecular weight which participates in biological electron transfer reactions through its heme cofactor. The protein has, from an examination of the crystal structure (code 1HRC—Protein Databank; 1.9 Å resolution), 19 surface-exposed lysine side-chain amino groups, the target of the acylating dye, and a single, surface sulfhydryl group (cysteine 17). The protein has a net charge of +9 at pH 7 and a maximum ground state dipole moment of 60 Debye calculated by using a standard program and the Charm charge set (Gunner et al., 1996 and references therein). Cytochrome c was covalently labeled with either an amine- or sulfhydryl-selective derivative of oxazole pyridinium, both of which carry a positive +1 charge, and purified by extensive dialysis according to prescribed procedure and previous work (Salafsky et al., 1996). The sulfhydryl-specific dye was 1-(2,3-epoxypropyl)-4-(5-(4-methoxyphenyl)oxazol-2-yl) pyridinium trifluoromethanesulfonate (PyMPO epoxide), and the amine-specific dye was 1-(3-(succinimidyloxycarbonyl) benzyl)-4-(5-(4-methoxyphenyl)oxazol-2-yl)pyridinium bromide (PyMPO, SE). Non-covalently bound dye could be completely removed by successive dialysis steps as established by a control experiment with a non-reactive oxazole dye. The degree of labeling could be determined by measuring the absorption spectrum of the protein-dye conjugate. Dye derivatives were obtained from Molecular Probes, and the parent compound has been shown to be highly SH-active at neutral pH (Salafsky and Eisenthal, 2000), the latter being of importance for biological studies. Protein was reacted with the dye at a 5:1 mole ratio (dye:protein) in distilled water (sulfhydryl-specific reaction) or sodium bicarbonate at pH 8.3 (amine-specific).

The second harmonic generation set-up has been described previously in detail (Eisenthal, 1996; and references therein). Briefly, the beam of an argon ion laser (10.5 W) is directed into the cavity of a titanium sapphire mode-locked laser (Tsunami). The output, at a repetition rate of 82 MHz with ~150 fs pulse duration (800–834 nm adjustable), was used as the fundamental light. The fundamental light was directed on to the reflecting plane of the water surface (double distilled water in a Teflon dish) at an angle of 70° to the surface normal, and was removed after the sample by a filter. Although the two-photon fluorescence of the dye is easily visible as a greenish-yellow glow, it is spectrally well-separated from the 2ω wavelength due to a Stokes shift of ~130 nm. In addition, the reflection set-up collects only a small portion of the light emitted, which further reduces the amount of detected fluorescence. The second harmonic light was collected and focused into a monochromator. For all experiments, the polarization of the fundamental was set to 45° from the normal to the laser table. Detection was accomplished using a photomultiplier tube in single photon-counting mode.

Results and Interpretation

The intensity of SH light generated from the air-water interface at the 2% peak was measured to be 50±12 counts per second. Cytochrome c has been shown previously to adsorb to the air-water interface (Kozarac et al., 1987). When cytochrome c (without dye label) was added to the water phase, even at a 5–10 mM concentration, the SH intensity from the interface either remained unchanged or diminished slightly, demonstrating that the heme cofactor does not contribute significantly to the SH signal through a $\chi^{(2)}$ process, as expected since the heme macrocycle is highly centrosymmetric. This finding is also consistent with previous work in which the fundamental wavelength was tuned across the heme absorption without effect on the SH signal.

Figure 2:
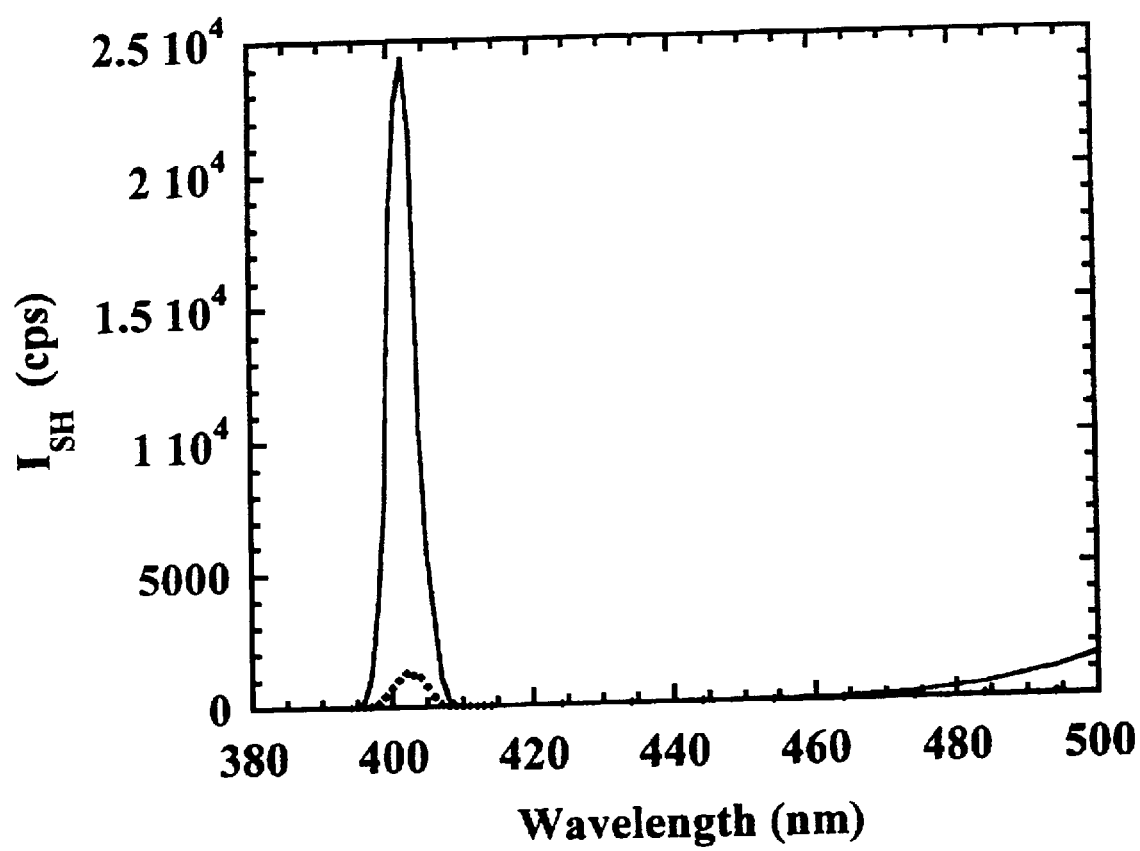
FIG. 2. The SH intensity spectrum of the cyt c-amine conjugate (1.5:1 dye:protein mole ratio; solid line) and cyt c-cysteine conjugate (0.4:1 dye:protein mole ratio; ♦♦♦ line) at the air-water interface at bulk concentrations of about 15 $\mu$M. The fundamental wavelength was set to 804 nm and the spectrum displays the characteristic 2ω peak. The tail of the two-photon fluorescence is visible in the spectrum of the amine conjugate. $I_{SH}$ (cps) is the intensity of SH light in counts per second.

A typical absorption spectrum of the dye-protein conjugate is shown in FIG. 1, along with spectra of the protein and dye separately. In FIG. 1, cytochrome (cyt) c is conjugated to an amine-reactive oxazole derivative and the degree of labeling is about 1.5:1 mole (dye:cyt) using the known extinction coefficients of the protein's heme group and the dye ($9.5 \times 10^4$ $M^{-1}$ $cm^{-1}$ at 412 nm and $2.6 \times 10^5$ $M^{-1}$ $cm^{-1}$ at 415 nm, respectively). At a concentration of 15 $\mu M$ in the subphase, the amine-labeled protein at the air-water interface produces a $2\omega$ signal of order $10^4$ cps (FIG. 2). The tail of the dye fluorescence is visible at about 480 nm and considerably smaller in magnitude than the SH peak. The SH signal of the cysteine-labeled cytochrome c was also measured (FIG. 2) and exhibits the same $2\omega$ peak as that of the amine conjugate, although the signal is smaller, around $10^3$ cps; this is expected given the smaller dye:protein labeling ratio (0.4:1 indicating about one dye every other protein) as measured from the conjugate's absorption spectrum.

Figure 3:
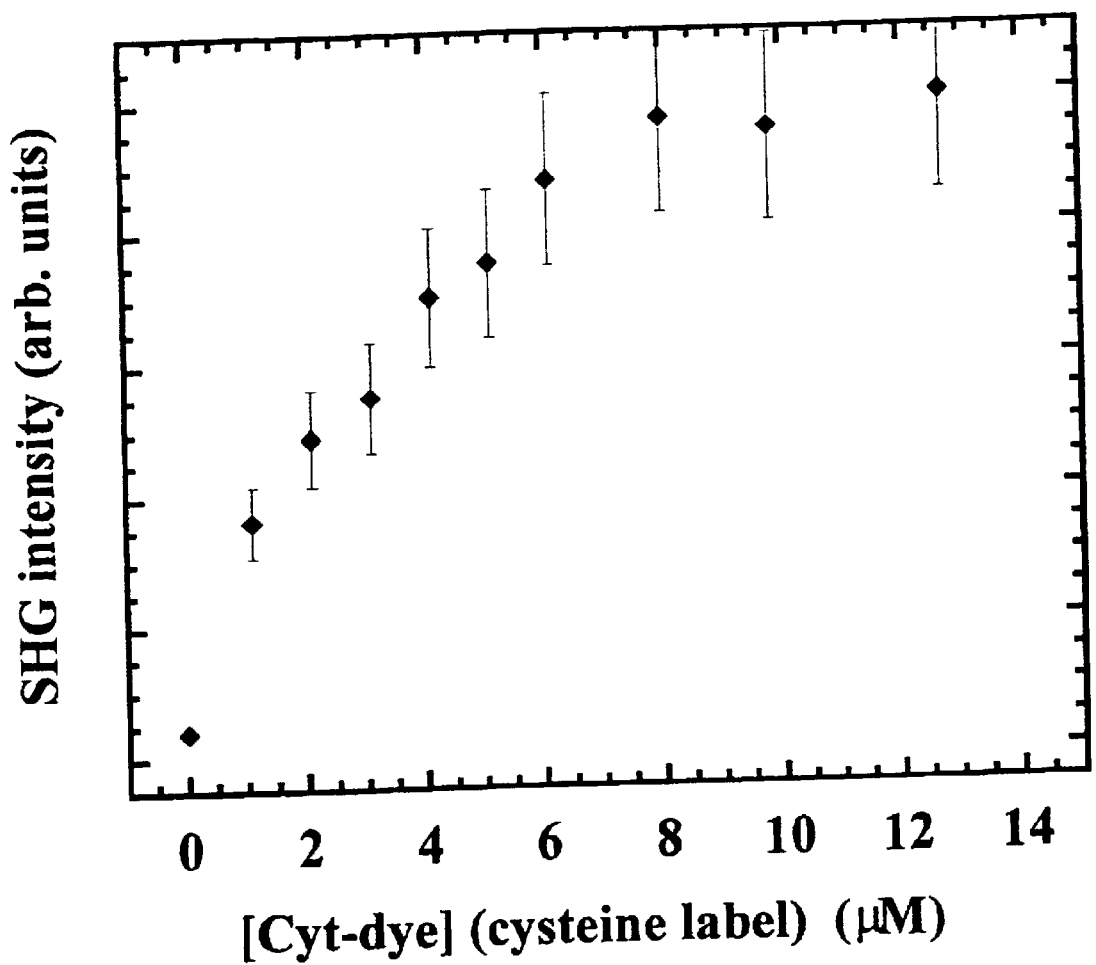
FIG. 3. Adsorption isotherm of the cysteine-cyt c conjugate (SH intensity vs. bulk [conjugate]) with error bars. The curve was fitted to a Langmuir adsorption model and, from this, a free energy of adsorption of $\Delta G = -11$ kcal/mole and the number of absorbates at the interface were determined.
Figure 4:
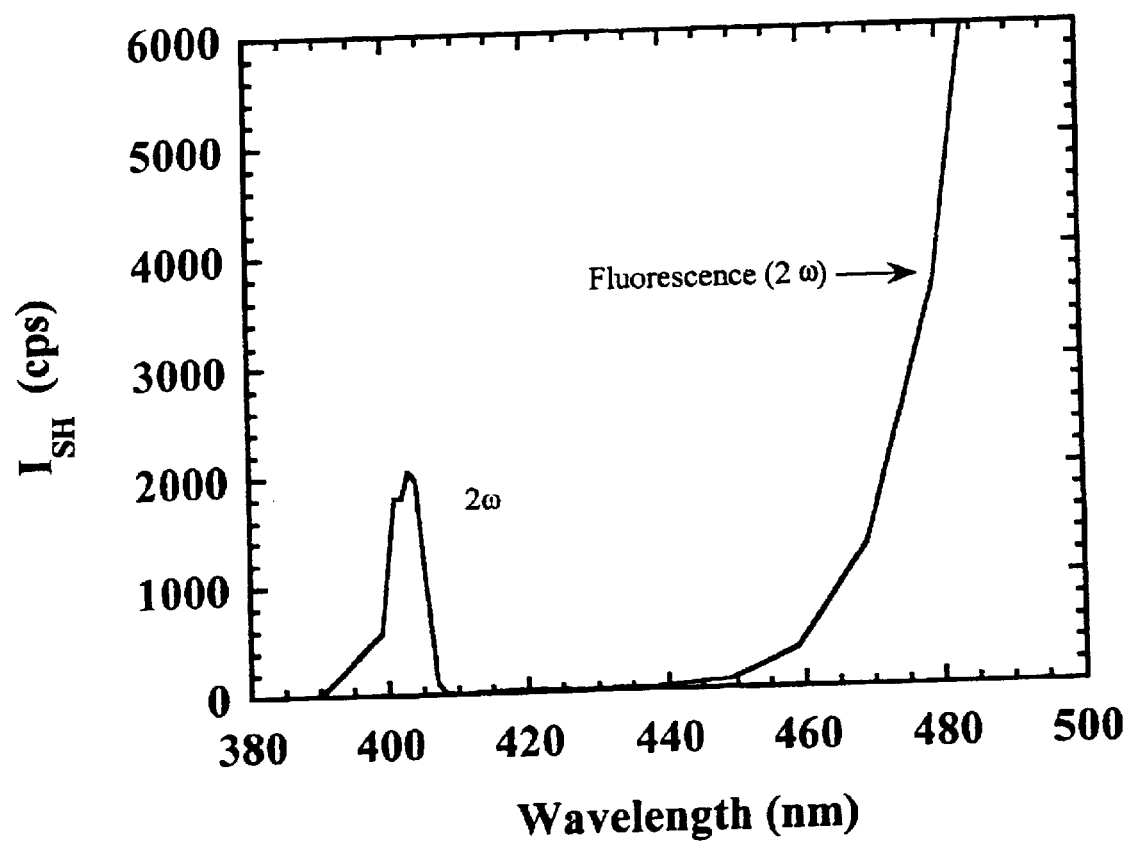
FIG. 4. SH intensity spectrum of the oxazole dye alone at the air-water interface. The bulk dye concentration is about 700 $\mu$M. Although the peak SH intensity is comparable to that for the cysteine conjugate, the bulk concentration of dye is at a factor of about 40 higher than that for either the cysteine or the amine conjugates. Accordingly, the (two photon) fluorescence background is much higher.

The orientation of the dye molecule in the cysteine conjugate was measured using a null angle technique (Salafsky and Eisenthal, 2000; Hicks, 1986). The SH light produced by this conjugate could be completely nulled by setting the analyzer at an angle of 30° from the surface normal, corresponding to a dye molecular orientation of 52° degrees from the normal under the assumption of a single hyperpolarizability element and a delta function in dye distribution. Because the dye orientation is measured with respect to the interfacial plane, an assumption of the dye's orientation on the surface of the protein must be made to determine the protein's orientation in the lab frame. If we assume that the dye is oriented so that its principal bond axis (and likely SH-active axis) lies normal to the protein's surface, from an examination of the x-ray crystal structure the cytochrome c is oriented so that the heme plane is about 30° degrees from the normal to the air-water interface, since the cysteine sulfhydryl group lies nearly in the plane of the heme. An adsorption isotherm of the cysteine conjugate was also measured at the air-water interface by adding small aliquots of the conjugate to the water subphase (FIG. 3). By fitting the data to a Langmuir isotherm (Eisenthal, 1996), the free energy of the conjugate's adsorption to the air-water interface could be determined to be $\Delta G=-11$ kcal/mole which indicates a strong surface activity. However, when the oxazole dye alone (+1 charge) was added to the water phase at the concentrations used for the conjugate (1–15 $\mu M$), it produced no detectable change in the background SH signal. Only at much higher concentrations of the dye (>0.5 mM) was the SH signal detectable, with an intensity of several thousand counts per second (FIG. 4). The free energy of the cytochrome adsorption to the air-water interface is therefore significantly larger than that for the free oxazole dye.

These results suggest the use of SHG-labels in other experiments. For instance, by designing an appropriate molecular platform at an interface—a supported lipid bilayer system, for example—one might use them to study protein-protein interactions at a membrane. Moreover, because SH light can be generated at non-planar surfaces (liposomes, for instance, where their diameter is ~$\lambda$, the wavelength of the fundamental light; see Srivastava and Eisenthal, 1998), they may also find use in studies involving the surface of liposomes or biological cells.

The present application has demonstrated the concept of a 'SHG-label': the labeling of some molecule of interest with a SH-active moiety for studying that molecule at an interface via a surface-selective technique such as second harmonic generation. As an illustration of the technique, the protein cytochrome c was covalently labeled with amine- and sulfhydryl-specific SH-active dyes in order to study the dye-protein conjugate at an air-water interface. Because of the SH-activity of the dye, the protein can be easily detected at the interface; if unlabeled, the protein is undetectable. Any protein of interest might thus be studied at an interface using a SHG-label. The label's chemical specificity, its SH cross-section, or its absorption and resonance wavelength can be changed in accordance with the demands of a particular requirement. SHG-labels for proteins should prove useful in studies of protein-receptor binding at interfaces of supported membranes, liposomes or cells. SHG-labeling should also prove useful for studies of other molecules including nucleic acids, lipids, carbohydrates, nanoparticles, and polymer systems.

References

Eisenthal, K. B. 1996. Photochemistry and Photophysics of Liquid Interfaces by Second Harmonic Spectroscopy. *J. Phys. Chem.* 100:12997–13006.

Gunner, M. R., Nicholls, A., Honig, B, J. 1996. Electrostatic Potentials in Rhodopseudomonas Viridis Reaction Centers: Implications for the Driving Force and Directionality of Electron Transfer. *J. Phys. Chem.* 100:4277–4291.

Heinz, T. F. 1991. Second Order Nonlinear Optical Effects at Surfaces and Interfaces. In Nonlinear Surface Electromagnetic Phenomena. Ponath, H. E. and Stegeman, G. I., editors. Elsevier/North Holland, Amsterdam. Chapter 5.

Hicks, J. M. 1986. Studies of Chemical Processes in Liquids Using Short Laser Pulses: 1. The Dynamics of Photoisomerization of Polar Molecules in Solution 2. Studies of Liquid Surfaces by Second Harmonic Generation Ph.D. dissertation, Columbia University.

Kozarac, Z., Dhathathreyan, A., Mobius, D. 1987. Interaction of Proteins with Lipid Monolayers at the Air-Solution Interface Studied by Reflection Spectroscopy. *Eur. Biophys. J.* 15:193–196.

Reider, G. A. and Heinz, T. F. 1995. Second-order Nonlinear Optical Effects at Surfaces and Interfaces In Photonic Probes of Surfaces. Halevia, P., editor. Elsevier Science, Amsterdam. Chapter 9.

Salafsky, J. S. and Eisenthal, K. B. 2000a. Second Harmonic Spectroscopy: Detection and Orientation of Molecules at a Biomembrane Interface. *Chem. Phys. Lett.* 319:435–439.

Salafsky, J. S. and Eisenthal, K. B. 2000b. Protein adsorption at interfaces detected by second harmonic generation. *J. Phys. Chem. B.* 104: 7752–7755.

Salafsky, J. S., Groves, J. T., Boxer, S. G. 1996. Architecture and Function of Membrane Proteins in Supported Lipid Bilayers: A Study with Photosynthetic Reaction Centers, *Biochemistry*. 35:14773–14781.

Shen, Y. R. 1984. The Principles of Nonlinear Optics, John Wiley & Sons, New York.

Shen, Y. R. 1989. Surface properties probed by second-harmonic and sum-frequency generation. *Nature* 337: 519–525.

Srivastava, A., Eisenthal, K. B. 1998. Kinetics of Molecular Transport Across a Liposome Bilayer, *Chem. Phys. Lett.*, 292:345–351.

What is claimed is:

1. A method for detecting a molecule which is labeled with a second harmonic-active label at an interface, which comprises:
   (a) contacting the labeled molecule with the interface such that the label has a net orientation at the interface;
   (b) detecting light emitted from the interface using a surface selective technique so as to detect the labeled molecule in contact with the interface,
   wherein an unlabeled molecule at the interface is undetectable using the surface selective technique, and wherein the second harmonic-active label is hyperpolarizable.

2. The method of claim 1, wherein the surface selective technique is second harmonic generation or sum-frequency generation.

3. The method of claim 1, wherein the molecule is a protein, a nucleic acid, a lipid, or a carbohydrate.

4. The method of claim 3, wherein the nucleic acid is a ribonucleic acid (RNA) or a deoxyribonucleic acid (DNA).

5. The method of claim 1, wherein the molecule is a pollutant.

6. The method of claim 1, wherein the molecule is on a surface of a nanoparticle or a polymer bead.

7. The method of claim 1, wherein the second harmonic-active label is bound to the molecule by a specific interaction or a non-specific interaction.

8. The method of claim 7, wherein the specific interaction comprises a covalent bond or a hydrogen bond.

9. The method of claim 7, wherein the non-specific interaction comprises an electrostatic interaction.

10. The method of claim 1, wherein the second harmonic-active label is specific for an amine group or a sulfhydryl group on the molecule.

11. The method of claim 1, wherein the second harmonic-active label comprises a plurality of individual second harmonic-active moieties which each have a nonlinear hyperpolarizability and are bound together in a fixed and determinate orientation with respect to each other so as to increase the overall nonlinear hyperpolarizability of the second harmonic-active label.

12. The method of claim 1, wherein the interface is at a membrane, a liposome, a cell surface, a viral surface, a bacterial surface, or a biosensor.

13. The method of claim 1, wherein the interface is a vapor-liquid interface, a liquid-liquid interface, a liquid-solid, or a solid-solid interface.

14. The method of claim 13, wherein the vapor-liquid interface is an air-water interface.

15. The method of claim 13, wherein the liquid-liquid interface is an oil-water interface.

16. The method of claim 13, wherein the liquid-solid interface is a water-glass interface or a benzene-$SiO_2$ interface.

17. The method of claim 1, wherein the molecule is a protein and the interface is at a receptor on a membrane.

18. The method of claim 1, wherein the molecule is on a viral surface and the interface is at a cell surface.

19. The method of claim 1, wherein the molecule is a protein and the interface is at a protein.

20. The method of claim 1, wherein the molecule is on a cell and the interface is at a cell surface.

21. A method for detecting a molecule in a medium, which comprises:
   (a) labeling a surface with a first molecule which is labeled with a second harmonic-active label, which is hyperpolarizable and at an interface wherein the first molecule specifically interacts with a second molecule to be detected,
   (b) contacting the surface with a medium comprising the second molecule, thereby creating an interface at the surface such that the label has a net orientation at the interface.
   (c) detecting the first molecule at the interface by measuring a signal generated by the second harmonic-active label using a surface selective technique, wherein an unlabeled molecule at the interface is undetectable using the surface selective technique, and
   (d) detecting a change in the signal when the second molecule interacts with the first molecule, thereby detecting the second molecule in the medium.

22. The method of claim 21, wherein the surface is on a nanoparticle or a polymer bead.

23. The method of claim 21, wherein the surface selective technique is second harmonic generation or sum-frequency generation.

24. The method of claim 21, wherein the molecule is a pollutant or a charged species.

25. The method of claim 24, wherein the pollutant is lead or polychlorinated biphenyl.

26. The method of claim 24, wherein the charged species is a chloride ion.

27. The method of claim 21, wherein the interaction between the second harmonic-active labeled molecule and the molecule to be detected is an antibody-antigen interaction.

28. The method of claim 21, wherein the medium contains an amount of the molecule to be detected, the change in the signal when the molecule interacts with the second harmonic-active labeled molecule is a quantitative change, and the amount of the molecule in the medium is determined from the change in the signal.

29. The method of claim 21, wherein the molecule to be detected is labeled with a second harmonic-active label.

30. A method for detecting an interaction between a first molecule which is labeled with a second harmonic-active label and a second molecule, which comprises:
   (a) contacting the first molecule at an interface with a medium comprising the second molecule such that the label has a net orientation at the interface wherein the first molecule specifically interacts with the second molecule; and
   (b) detecting an interaction between the first molecule and the second molecule at the interface by measuring a signal generated by the second harmonic-active label using a surface selective technique, wherein an unlabeled molecule at the interface is undetectable using the surface selective technique, and wherein the second harmonic-active label is hyperpolarizable.

31. The method of claim 30, wherein said second molecule is labeled with a second harmonic-active label.

32. The method of claim 21, wherein the first molecule or the second molecule is selected from the group consisting of a lipid, carbohydrate, protein and nucleic acid.

33. The method of claim 30, wherein the first molecule or the second molecule is selected from the group consisting of a lipid, carbohydrate, protein and nucleic acid.

34. The method of claim 1, wherein the interface is a cell surface and the labeled molecule is prepared outside of the cell.

* * * * *